United States Patent
Akita et al.

(10) Patent No.: US 6,242,255 B1
(45) Date of Patent: Jun. 5, 2001

(54) PROTEIN WHICH INDUCES INTERFERON-GAMMA PRODUCTION BY IMMUNOCOMPETENT CELL

(75) Inventors: Kenji Akita; Yoshiyuki Nukada; Mitsukiyo Fujii; Tadao Tanimoto; Masashi Kurimoto, all of Okayama (JP)

(73) Assignee: Kabushiki Kaisha Hayashibara Seibutsu Kegaku Kenkyujo, Okayama (JP)

(*) Notice: Subject to any disclaimer, the term of this patent is extended or adjusted under 35 U.S.C. 154(b) by 0 days.

(21) Appl. No.: 08/832,198

(22) Filed: Apr. 8, 1997

Related U.S. Application Data (62) Division of application No. 08/721,018, filed on Sep. 26, 1996, now abandoned.

(30) Foreign Application Priority Data

Sep. 26, 1995 (JP) ...................................... 7-270725
Feb. 29, 1996 (JP) ...................................... 8-067434
Sep. 20, 1996 (JP) ...................................... 8-269105

(51) Int. Cl.[7] ...................................... C12N 5/08

(52) U.S. Cl. .............................. 435/366; 435/325; 514/2; 514/21; 530/324; 530/350

(58) Field of Search ................... 514/12, 15, 14, 514/2, 21; 530/300, 350, 412, 324; 435/68.1, 69.1, 252.3, 320.1, 325, 366; 536/23.1, 23.5; 424/85.2

(56) References Cited

U.S. PATENT DOCUMENTS 5,879,942 * 3/1999 Tanimoto et al. ............... 435/226
5,891,662 * 4/1999 Tanimoto et al. ............... 435/69.1
6,060,283 * 5/2000 Okura et al. ................... 435/69.52

FOREIGN PATENT DOCUMENTS

| 0692536 | 1/1996 | (EP) . |
| 0712931 | 7/1996 | (EP) . |
| 2016015 | 9/1979 | (GB) . |
| 8-027189 | 1/1996 | (JP) . |
| 8-193098 | 7/1996 | (JP) . |
| 9205256 | 4/1992 | (WO) . |

OTHER PUBLICATIONS

Genbank/dbEST: Public Availability Dates for—SEQ ID NOS : 2–7 of the instant application and the database alignments, Sep. 14, 1995.*
Schoenhaut et al. J. Immunol. 148 : 3433–40, Jun. 1, 1992.*
H. Okamura et al., "Cloning of a new cytokine that induces IFN–Gamma", Letters To Nature, vol. 378, pp. 88–91, Nov. 2, 1995.
K. Nakamura et al., "Purification of a Factor Which Provides a Costimulatory Signal for Gamma Interferon Production", Infection And Immunity, vol. 61, No. 1, pp. 64–70, Jan. 1993.
Okamura et al. Nature 378 : 88–91, Nov. 2, 1995.*
Hatt, Harold D. ed. et al., "American Type Culture Collection Catalogue of Cell Lines and Hybridomas." 5th ed., (1985).
Kostura, Matthew J. et al., "Identification of a Monocyte Specific Pre–interleukin 1β Convertase Activity." Proc. Natl. Acad. Sci., vol. 86, pp. 5227–5231 (Jul. 1989).

(List continued on next page.)

Primary Examiner—Jeffrey Stucker
Assistant Examiner—Jegatheesan Seharaseyon
(74) Attorney, Agent, or Firm—Browdy & Neimark (57) ABSTRACT

A protein of human cell origin, which induces the IFN-γ production by immunocompetent cells and has the amino acid sequence of SEQ ID NO:1 near or at the N-terminus. It can be produced from human cells such as lymphoblasts, lymphocytes, monoblasts, monocytes, myeloblasts, myelocytes, granulocytes and macrophages, and used for preventing and/or treating IFN-γ susceptive diseases.

5 Claims, 1 Drawing Sheet

OTHER PUBLICATIONS

Fujioka, T. et al., "Combination of Lymphokine–activated killer cells and interleukin–2 in treating metastatic renal cell carcinoma." British Journal Of Urology, vol. 73, pp. 23–31 (1994).

Laemmli, U.K., "Cleavage of Structural Proteins during the Assembly of the Head of Bacteriophage T4." Nature, vol. 227, pp. 680–685 (Aug. 15, 1970).

Balkwill, Francis R., "Cytokines in Cancer Therapy." Oxford University Press, New York, New York, (1989).

Ushio, S. et al., "Cloning of the cDNA for Human IFN–gamma–inducing Factor", Journal Of Immunology, vol. 156, No. 11, pp. 4274–4279, Jun. 1, 1996.

* cited by examiner

FIG.1

PROTEIN WHICH INDUCES INTERFERON-GAMMA PRODUCTION BY IMMUNOCOMPETENT CELL

This is a division of copending parent application Ser. No. 08/721,018 filed Sep. 26, 1996 now abandoned.

BACKGROUND OF THE INVENTION

1. Field of the Invention

The present invention relates to a novel protein which induces the interferon-γ (hereinafter abbreviated as "IFN-γ") production by immunocompetent cells.

2. Description of the Prior Art

It is known that IFN-γ is a protein which has antiviral-, antioncotic- and immunoregulatory-activities and is produced by immunocompetent cells that are stimulated with antigens or mitogens. Because of these biological activities, IFN-γ has been expected for use as an antitumor agent since it was discovered, and studied energetically on clinical trials as a therapeutic agent for malignant tumors in general including brain tumors. IFN-γ preparations commercially available now are roughly classified into two groups, i.e. one group of natural IFN-γs produced by immunocompetent cells and another group of recombinant IFN-γs produced by transformants obtained by introducing DNAs which encode natural IFN-γs into microorganisms of the species *Escherichia coli*. In the above clinical trials, one of these two groups of IFN-γs is administered to patients as an "exogenous IFN-γ".

Among these IFN-γs, natural IFN-γs are usually produced by culturing established immunocompetent cell lines in nutrient culture media admixed with IFN-γ inducers to produce IFN-γs, and purifying the produced IFN-γs from the resulting cultures. It is known that IFN-γ inducers greatly influences on the IFN-γ yield, the facility of IFN-γ purification, and the safety of final IFN-γ preparations. Generally, mitogens such as concanavalin A (Con A), lentil lectin, pokeweed lectin, endotoxin and lipopolysaccharides can be used as IFN-γ inducers. However, these mitogens have the following problems: (i) their molecules and qualities vary and change depending on their origins and purification methods, and (ii) preparations with a constant IFN-γ inducibility are not readily prepared in a satisfactory yield. In addition, most of these mitogens might induce unfavorable side effects when administered to living bodies, and some of them might cause toxicity, so that it is substantially difficult to induce IFN-γ production by directly administering IFN-γ inducers to the living bodies.

SUMMARY OF THE INVENTION

The present invention was made based on a novel protein which induces the interferon-γ production by immunocompetent cells. During the study of cytokines produced by mammalian cells, the present inventors noticed that the existence of a substance which induces IFN-γ production in mouse liver cells which had been treated with a lipopolysaccharide and inactivated whole cells of Corynebacterium. They isolated the substance by many purification methods using column chromatography as a main technique and studied the properties and features, and have found that the reality is a protein having the following physicochemical properties:

(1) Molecular weight 19,000±5,000 daltons on sodium dodecyl sulfate polyacrylamide gel electrophoresis (SDS-PAGE);

(2) Isoelectric point (pI) pI of 4.8±1.0 on chromatofocusing;

(3) Partial amino acid sequence Having the partial amino acid sequences of SEQ ID NOs:8 and 9; and (4) Biological activity Inducing the IFN-γ production by immunocompetent cells.

The data concluded that the substance is novel because no protein with these physicochemical properties is known. The present inventors continued studying on mouse liver cells and have succeeded to isolate a DNA which encodes the protein. The inventors decoded the DNA and have found that it consists of 471 base pairs and encodes the amino acid sequence of SEQ ID NO:10 (where the symbol "Xaa" means "methionine" or "threonine").

Based on these findings, the present inventors further studied on human liver cells to obtain a DNA which encodes another novel substance that induces the IFN-γ production by immunocompetent cells. They revealed that the reality is a polypeptide, then decoded the DNA and found that it has the amino acid sequence of SEQ ID NO:6 (where the symbol "Xaa" is "isoleucine" or "threonine"). They introduced the DNA into *Escherichia coli* to express the polypeptide and to produce it in the resulting culture in a satisfactorily high yield. These findings were disclosed in Japanese Patent Laid-Open Nos.27,189/96 and 193,098/96, applied by the present applicant. In Japanese Patent Application No.78, 357/95 applied by the applicant, the polypeptide is disclosed as an agent for susceptive diseases. Although biologically active proteins which are administered to humans after mixed with pharmaceuticals should be generally human cell origin, no human cell which produces such a polypeptide is reported.

In view of the foregoing, the object of the present invention is to provide a protein of human cell origin, which induces the IFN-γ production by immunocompetent cells.

The another object of the present invention is to provide a process for producing the protein.

The further object of the present invention is to provide the use of the protein as an agent for susceptive diseases.

The first object of the present invention is attained by a protein of human cell origin which induces the IFN-γ production by immunocompetent cells and has the amino acid sequence of SEQ ID NO:1.

The second object of the present invention is attained by a process for producing the protein by propagating human cells which produce the protein, and collecting the protein from the propagated cells.

The third object of the present invention is attained by an agent for susceptive diseases, which contains the protein as an effective ingredient.

DETAILED DESCRIPTION OF THE INVENTION

The protein according to the present invention induces the IFN-γ production by immunocompetent cells when allowed to act on the cells alone or together with an appropriate cofactor.

The protein is derived from human cells, and it can be readily prepared by the present process using human cells.

The agent for susceptive diseases according to the present invention induces the IFN-γ production by immunocompetent cells in the human body when administered to humans, and exerts positive effects in the treatment and prevention of IFN-γ susceptive diseases. When the protein augments the cytotoxicity of killer cells or induces the formation of killer cells, it exerts positive effects on inveterate diseases including malignant tumors.

The preferred embodiments according to the present invention will be described hereinafter. The wording "protein" as referred to in the present invention means polypeptides and glycoproteins in general which induce the IFN-γ production by immunocompetent cells and have the amino acid sequence of SEQ ID NO:1. Depending on the types and propagation conditions of human cells, the protein has the amino acid sequences of SEQ ID NOs:1 and 3 near at the N- and C-termini, respectively, and occasionally has the amino acid sequence of SEQ ID NO:6, as a complete amino acid sequence, including the amino acid sequences of SEQ ID NOs:4 and 5 as an internal fragment (where the symbol "Xaa" means "isoleucine" or "threonine"). The protein is detected as a protein band at a position corresponding to a molecular weight of 14,000–24,000 daltons, usually, 18,000–19,500 daltons when determined on sodium dodecyl sulphate polyacrylamide gel electrophoresis (SDS-PAGE) in the presence of a reducing agent. Depending on the types and propagating conditions of human cells, one or more amino acids may be added to the above N- and/or C-termini of SEQ ID NOs:1 and 3 or one or more amino acids in the N- and/or C-termini may be deleted. Any protein can be used in the present invention as long as it is derived from a human cell, as well as having either of these amino acid sequences and inducing the IFN-γ production when acting on immunocompetent cells alone or together with an appropriate cofactor.

These proteins can be produced by the present process using human cells. Usually, the human cells used in the present invention include cell lines derived from human hematopoietic cells such as lymphoblasts, lymphocytes, monoblasts, monocytes, myeloblasts, myelocytes, granulocytes and macrophages. Examples of these cell lines are lymphomas and leukemias such as myelocytic leukemia, promyelocytic leukemia, adult T-cell leukemia, and hairy cell leukemia, specifically, HBL-38 cell, HL-60 cell (ATCC CCL240), K-562 (ATCC CCL243), KG-1 cell (ATCC CCL246), Mo cell (ATCC CRL8066), THP-1 cell (ATCC TIB202), and U-937 cell (ATCC CRL1593) as reported by Jun MINOWADA in "Cancer Review", Vol.10, pp.1–18 (1988), and A-253 cell (ATCC HTB41), an epidermoid carcinoma, submaxillary gland, human. Mutants of these cell lines can be also used in the present invention. Because these cell lines readily proliferate and more produce the present protein, they can be advantageously used in the present invention. Especially, epidermoid carcinoma cell lines such as A-253 cell, and human myelomonocytic cell lines such as HBL-38 cell, HL-60 cell, KG-1 cell, THP-1 cell, and U-937 cell have an extremely high productivity of the present protein and are most satisfactorily used in the present invention.

In the present process, the above human cells are first allowed to propagate, then the present protein is collected from the propagated cells. The method used to propagate these human cells in the present invention is not specifically restricted, and any conventional in vitro or in vitro propagation method can be used. The in vitro propagation method means a method to propagate cells using nutrient culture media, which comprises suspending human cells in RPMI 1640 medium, MEM medium and DEM medium, which are used conventionally to propagate animal cells in this field, supplemented with 0.3–30 w/v % of fetal bovine serum to give a cell density of about $1\times10^4$–$1\times10^7$ cells/ml, preferably, about $1\times10^5$–$1\times10^6$ cells/ml, and culturing these cells at a temperature of 36–38° C., preferably, a temperature of about 37° C. and at a pH of 7–8, preferably, a pH of 7.2–7.4, for about 1–7 days while replacing these media with fresh ones. Thereafter, the propagated cells were separated from the cultures to obtain the objective protein. Depending on the types and culture conditions of human cells, some cells extracellularly excrete the present protein while culturing. When coexisted in culture media inducers such as mitogens and/or IFN-γs which induce the production of the present protein by the human cells, most of or all of the protein may be produced extracellularly. In this case, the protein can be collected from the culture supernatants.

The in vivo propagation method for human cells using warm-blooded animals excluding human comprises injecting to suppress the immunoreaction of the animals antilymphocyte antibodies derived from rabbits into rodents such as new born mice, nude mice, rats, nude rats, guinea pigs, and hamsters, injecting subcutaneously or intraperitoneally about $1\times10^5$–$1\times10^8$ cells/animal of the human cells into the animals or placing the human cells in diffusion chambers embedded in or out of the animals' body while allowing the animals' body fluid to circulate in the chambers, and feeding the animals by conventional methods for about 2–10 weeks. During the feeding, the human cells propagate while receiving the animals' body fluid. The propagated human cells are collected in the form of a tumor mass, ascites or cell suspension. If necessary, the objective protein is collected after suspending and washing these human cells in and with an appropriate solvent. The in vivo propagation method has a merit that as compared with the in vitro propagation method it yields the present protein at a less labor cost and time and in a satisfactorily high yield. The in vivo propagation method is disclosed, for example, in Japanese Patent Publication No.54,158/81.

To collect the present protein from the propagated cells, these cells are disrupted by ultrasonic before or after separating the objective protein from the cultures, homogenizing, freezing and thawing, or by soaking these cells in considerably-low osmotic solvents, then the protein is collected from the resulting cell debris or from a mixture of cell debris and culture supernatant. To collect the protein from the cell debris or the mixture, the cell debris or the mixture can be subjected directly or after incubation at about 37° C. for 1–24 hours to the following conventional methods for purifying biologically active substances in this field: salting out, dialysis, filtration, concentration, separatory sedimentation, gel filtration chromatography, ion-exchange chromatography, hydrophobic chromatography, adsorption chromatography, affinity chromatography, chromatofocusing, gel electrophoresis and/or isoelectrophoresis. Two or more of these conventional methods can be selectively used in combination. The collected protein can be concentrated and/or lyophilized into a liquid or solid form to meet to final use. The monoclonal antibody as disclosed in Japanese Patent Application No.58,240/95 applied by the present applicant is advantageously used to purify the present protein. Immunoaffinity chromatography using the monoclonal antibody yields the highest possible purity of the protein at the lowest cost and labor.

As is described above, the protein according to the present invention has a property of inducing the IFN-γ production by immunocompetent cells. Thus it can be satisfactorily used as an inducer for IFN-γ production by cell culture methods and used in the treatment and prevention of IFN-γ susceptive diseases including viral diseases such as AIDS and condyloma acuminatum; malignant tumors such as malignant nephroma, granuloma, mycosis fungoides, and brain tumor; and immunopathies such as articular rheumatism and allergosis.

The present protein is usually added to nutrient culture media for IFN-γ production by culturing immunocompetent cells or administering to humans to treat and/or prevent IFN-γ susceptive diseases. In the former case, leukocytes separated from mammalian peripheral blood and established cell lines of immunocompetent cells such as HBL-38 cell, Mo cell (ATCC CRL8066), Jurkat cell (ATCC CRL8163), HuT78 cell (ATCC TIB161), EL4 cell (ATCC TIB39), L12-R4 cell, and mutants thereof are suspended in culture media containing about 0.1–1,000 ng/ml of the present protein, preferably, about 1–100 ng/ml of the protein. If necessary, these cells are cultured in nutrient culture media supplemented with T-cell stimulants such as mitogen, interleukin 2, and anti-CD3 antibody for about 1–100 hours in conventional manner while replacing the culture media with fresh ones. From the resulting cultures the present protein can be collected by one or more conventional methods used to purify IFN-γ such as salting out, dialysis, filtration, concentration, separatory sedimentation, gel filtration chromatography, ion-exchange chromatography, hydrophobic chromatography, adsorption chromatography, affinity chromatography, chromatofocusing, gel electrophoresis and isoelectrophoresis.

Because the present protein induces the IFN-γ production by human immunocompetent cells, agents for susceptive diseases containing the protein as an effective ingredient stimulate the human immunocompetent cells to produce IFN-γ by administering to humans, and exert positive effects on the treatment and/or the prevention of IFN-γ susceptive diseases. Killer cells participate in the treatment and/or the prevention of susceptive diseases when the present protein induces the IFN-γ production by immunocompetent cells, accelerates the cytotoxicity of killer cells such as cytotoxic T-cells and lymphokine activating killer cells including NK- and LAK-cells, and induces the formation of killer cells similarly as the proteins in the later described Experiments and Examples. The wording "susceptive diseases" as referred to in the present invention means diseases in general including IFN-γ susceptive diseases, which can be treated and/or prevented by IFN-γs and/or killer cells: For example, viral diseases such as hepatitis, herpes, condyloma acuminatum, and AIDS; infectious diseases such as candidiasis, malaria, cryptococcosis, and Yersinia; malignant solid tumors such as malignant tumor, mycosis fungoides, and chronic granulomatous disease; hematopoietic malignant tumors such as adult T-cell leukemia, chronic myelocytic leukemia, and malignant tumor; and immunopathies such as allergosis and rheumatism. When used with interleukin 3, the present protein positively effects on the complete cure or the remission of leukopenia and thrombocytopenia induced by radio- and chemo-therapies to treat leukemia, myeloma, and malignant tumors.

The present agent for susceptive diseases is widely used in the treatment and/or the prevention of the above susceptive diseases as an antitumor agent, antiviral agent, antiseptic, immunotherapeutic agent, platelet-increasing agent, or leukocyte-increasing agent. Depending on the type of agent and the symptom of susceptive diseases to be treated, the present agent is generally processed into a liquid, paste or solid form which contains 0.000001–100 w/w %, preferably, 0.0001–0.1 w/w % of the protein, on a dry solid basis (d.s.b.).

The present agent can be used intact or processed into compositions by mixing with physiologically-acceptable carriers, adjuvants, excipients, diluents and/or stabilizers, and, if necessary, further mixing with one or more other biologically-active substances such as interferon-a, interferon-β, interleukin 2, interleukin 3, interleukin 12, TNF-α, TNF-β, carboquone, cyclophosphamide, aclarubicin, thiotepa, busulfan, ancitabine, cytarabine, 5-fluorouracil, 5-fluoro-1-(tetrahydro-2-furyl)uracil, methotrexate, actinomycin D, chromomycin $A_3$, daunorubicin, doxorubicin, bleomycin, mitomycin C, vincristine, vinblastine, L-asparaginase, radio gold colloidal, Krestin®, picibanil, lentinan, and Maruyama vaccine. Among these combinations, a combination of the present protein and interleukin 2 is especially useful because interleukin 2 acts as a cofactor for the protein when the protein induces the IFN-γ production by immunocompetent cells. Another combination of the protein and a natural or recombinant human interleukin 2 induces a relatively high level of IFN-γ production with only a small amount of the protein which does not substantially induce the IFN-γ production by immunocompetent cells. While a combination of the protein and interleukin 12 induces a greater level of IFN-γ production which could not be readily attained by them each. Because the present protein increases the activity of interleukin 12 to inhibit the production of immunoglobulin E antibody in the human body, the protein is advantageously used as an agent for immunopathies such as atopic diseases including atopic asthma, atopic bronchial asthma, hay fever, allergic rhinitis, atopic dermatitis, angioedema, and atopic digestive system's disorder. Occasionally a relatively small amount of interleukin 12 exists in humans. In this case, a sole administration of the protein to humans can attain the desired effect.

The form of the present agent for susceptive diseases includes those in a unit dose form which means a physically formulated medicament suitable for administration and contains the protein in an amount from 1/40 to several folds, i.e. up to 4 folds of a dosage. Examples of these are injections, liquids, powders, granules, tablets, capsules, sublinguals, ophthalmic solutions, nasal drops, and suppositories.

The present agent can be orally or parenterally administered to patients, and as described below it can be used to activate antitumor cells in vitro. In both administrations, the agent exerts a satisfactory effect in the treatment and/or the prevention of susceptive diseases. Varied depending on the types of susceptive diseases and the symptoms of patients before and after the administration, the agent is orally administered to them or parenterally administered to their intradermal- and subcutaneous-tissues, muscles, and veins at a dose of about 0.1 μg to 50 mg per shot, preferably, about one μg to one mg per shot, 1–4 times/day or 1–5 times/week, for one day to one year.

The present agent can be also used in so called "antitumor immunotherapy" using interleukin 2. Generally, the antitumor immunotherapy is roughly classified into (i) a method for directly administering interleukin 2 to patients with malignant tumors, and (ii) a method for introducing antitumor cells which are previously activated in vitro by interleukin 2, i.e. an adoptive immunotherapy. The present protein significantly enhances the above immunotherapeutic effect by interleukin 2 when used in combination. In the method (i), the protein is administered to patients in an amount of about 0.1 μg/shot/adult to one mg/shot/adult at 1–10 times before the administration of interleukin 2 or at the same time. The dose of interleukin 2 is generally about 10,000–1,000,000 units/shot/adult, though it varies depending on the types of malignant tumors, patients' symptoms, and the dose of the present protein. In the method (ii), mononuclear cells and lymphocytes, collected from patients with malignant tumors, are cultured in the presence of interleukin 2 and about 0.1 ng to one µg of the protein per $1\times10^6$ cells of the blood cells. After culturing for a prescribed period of time, NK cells or LAK cells are collected from the culture and introduced into the same patients. Diseases which can be treated by the present antitumor immunotherapy are, for example, hematopoietic malignant tumors such as leukemia and malignant lymphoma, and solid malignant tumors such as colonic cancer, rectal cancer, large intestinal cancer, gastric cancer, thyroid carcinoma, cancer of the tongue, bladder carcinoma, choriocarcinoma, hepatoma, prostatic cancer, carcinoma uteri, laryngeal, lung cancer, breast cancer, malignant melanoma, Kaposi's sarcoma, cerebral tumor, neuroblastoma, tumor of the ovary, testicular tumor, osteosarcoma, cancer of the pancreas, renal cancer, hypernephroma, and hemangioendothelioma.

The following experiments explain the present protein:

EXPERIMENT 1
Preparation of Protein

New born hamsters were suppressed their immunoreaction in conventional manner by injecting a rabbit antiserum to hamster antithymus into the hamsters, transplanted to their dorsal subcutaneous tissues with about $5\times10^5$ cells/hamster of THP-1 cells (ATCC TIB202), a myelomonocytic cell line of a human acute monocytic leukemia, and fed for 3 weeks in conventional manner. Tumor masses formed in their subcutaneous tissues, about 15 g weight per hamster, were extracted, dispersed in conventional manner in physiological saline, and washed with phosphate buffered saline (hereinafter abbreviated as "PBS").

The propagated cells thus obtained were washed with 10-fold volumes of cold 20 mM Hepes buffer (pH 7.4) containing 10 mM potassium chloride, 1.5 mM magnesium chloride, and 0.1 mM disodium ethylenediaminetetraacetate, allowed to stand in 3-fold volumes of a fresh preparation of the same buffer under ice-chilled conditions, freezed at −80° C., and thawed to disrupt the cells. The disrupted cells were centrifuged to obtain a supernatant which was then fed to a column packed with "DEAE-SEPHAROSE", a gel for ion-exchange column chromatography commercialized by Pharmacia LKB Biotechnology AB, Uppsala, Sweden, which had been previously equilibrated with 10 mM phosphate buffer (pH 6.6), followed by washing the column with 10 mM phosphate buffer (pH 6.6), feeding to the column with a gradient buffer of sodium chloride which increases stepwisely from 0 M to 0.5 M in 10 mM phosphate buffer (pH 6.6), and collecting a fraction eluted at about 0.2 M sodium chloride.

The fraction was dialyzed against 10 mM phosphate buffer (pH 6.8) and fed to a column packed with "DEAE 5PW", a gel for ion-exchange chromatography commercialized by Tosoh Corporation, Tokyo, Japan, followed by feeding to the column a gradient buffer of sodium chloride which increases stepwisely from 0 M to 0.5 M in 10 mM phosphate buffer (pH 6.8), and collecting fractions eluted at about 0.2–0.3 M sodium chloride.

The resulting fractions were pooled, then dialyzed against PBS, fed to a plastic cylindrical column packed with a gel for immunoaffinity chromatography using a monoclonal antibody which had been prepared according to the method as disclosed in Japanese Patent Application No.58,240/95 applied by the present applicant, and washed with PBS. The column was fed with 100 mM glycine-HCl buffer (pH 2.5) to collect from the eluate fractions containing a protein which induces the IFN-γ production by immunocompetent cells. These fractions were pooled, dialyzed against sterile distilled water, concentrated with a membrane filter, and lyophilized to obtain a purified solid protein in a yield of about 50 ng per hamster.

EXPERIMENT 2
Molecular Weight

In accordance with the method reported by U. K. Laemmli in *Nature*, Vol.227, pp.680–685 (1970), a purified protein prepared by the method in Experiment 1 was electrophoresed on a sodium dodecyl sulfate polyacrylamide gel (SDS-PAGE) in the presence of 2 w/v % dithiothreitol, resulting in a main protein band with an IFN-γ inducibility at a position corresponding to about 18,000–19,500 daltons. The marker proteins used in this experiment were bovine serum albumin (MW=67,000 daltons), ovalbumin (MW=45,000 daltons), carbonic anhydrase (MW=30,000 daltons), soy bean trypsin inhibitor (MW=20,100 daltons), and α-lactalbumin (MW=14,400 daltons).

EXPERIMENT 3
Amino Acid Sequence and Peptide Mapping Near at the N-terminus

EXPERIMENT 3-1
Amino Acid Sequence Near at the N-terminus

The purified protein in Experiment 1 was analyzed on "MODEL 473A", a protein sequencer commercialized by Perkin-Elmer Corp., Instrument Div., Norwalk, USA, and revealed that it has the amino acid sequence of SEQ ID NO:1, particularly, SEQ ID NO:2.

EXPERIMENT 3-2
Peptide Mapping

A purified protein obtained by the method in Experiment 1 was dissolved in an adequate amount of sterile distilled water, and the solution was fed to a column packed with "ASAHIPAK® C4P-50 4E", a gel for high-performance liquid chromatography (HPLC) commercialized by Showa Denko, K. K., Tokyo, Japan, which had been previously equilibrated with 0.1 v/v % aqueous trifluoroacetic acid solution, followed by washing the column with 0.1 v/v % aqueous trifluoroacetic acid solution and feeding to the column a linear gradient solution of acetonitrile increasing from 0 v/v % to 90 v/v % in a mixture solution of trifluoroacetic acid and acetonitrile at a flow rate of 60 ml/hour. Fractions containing a protein which induces the IFN-γ production by immunocompetent cells were collected from the eluted fractions, pooled, neutralized with 1 M aqueous tris solution (pH 11.2), and concentrated in conventional manner. To 50 mM Tris-HCl buffer (pH 8.5), dissolving an adequate amount of clostripain commercialized by Sigma Chemical Company, St. Louis, Mo., USA, was added the protein in an amount of about 50 folds of the clostripain by molar ratio while removing acetonitrile, and the resulting mixture was allowed to react at a pH of 8–9 and at 37° C. for 12 hours to obtain a reaction mixture containing fragments of the protein.

Figure 1:
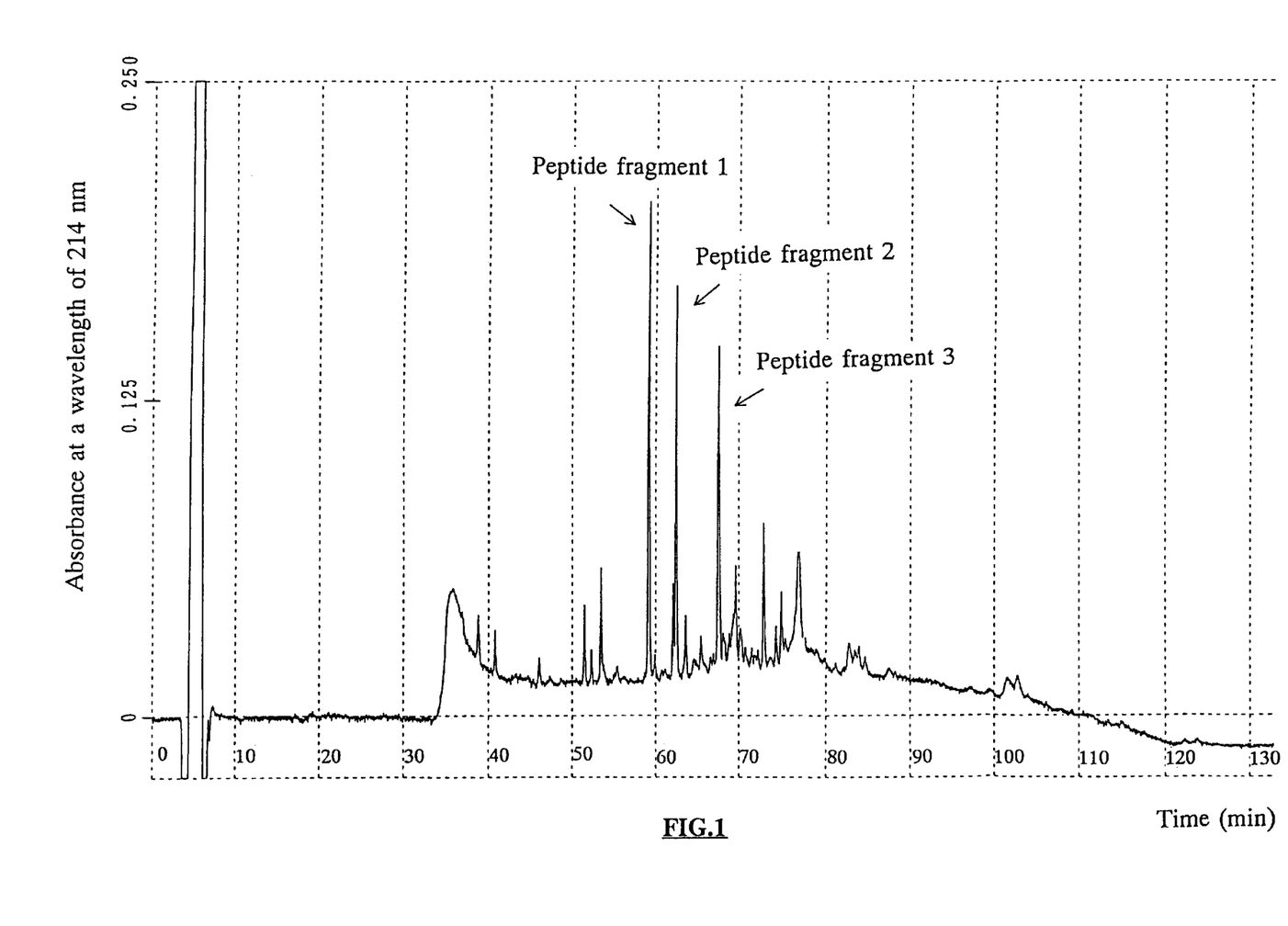
FIG. 1 is a peptide map of the present protein.

The reaction mixture was fed to a column packed with "ODS-120T", a gel for HPLC commercialized by Tosoh Corporation, Tokyo, Japan, which had been previously equilibrated with 0.1 v/v % aqueous trifluoroacetic acid solution, followed by washing the column with 0.1 v/v % aqueous trifluoroacetic acid solution and feeding to the column a linear gradient solution of acetonitrile increasing from 0 v/v % to 70 v/v % in a mixture solution of trifluoroacetic acid, acetonitrile and water where the concentration of trifluoroacetic acid was 0.09 v/v % at a flow rate of 30 ml/hour while monitoring the absorption level of the peptide, i.e. the concentration of the peptide, at a wave length of 214 nm. FIG. 1 is the resulting peptide map.

In FIG. 1, peptide fragments eluted at about 59, 62 and 68 min after initiating the elution are respectively named peptide fragments 1, 2 and 3. These peptide fragments were separatory collected and analyzed for amino acid sequence on "MODEL 473A", a protein sequencer commercialized by Perkin-Elmer Corp., Instrument Div., Norwalk, USA, in conventional manner. As a result, it was revealed that the peptide fragments 1 and 2 have the amino acid sequences of SEQ ID NOs:3 and 7, respectively, while the peptide fragment 3 has those of SEQ ID NOs:4 and 5. The comparison of these amino acid sequences with the one of SEQ ID NO:6 revealed that the peptide fragments 1 to 3 correspond to the positions 148–157, 1–13 and 45–58 or 80–96 in the amino acid sequence of SEQ ID NO:6, respectively. These results confirmed that the peptide fragments 1 and 2 correspond to the C- and N-terminal fragments of the protein used for analysis, and the peptide fragment 3 corresponds to an internal fragment of the protein.

It is concluded that the purified protein obtained by the method in Experiment 1 contains the amino acid sequence of SEQ ID NO:6 when totally evaluating these results, the fact as revealed in Experiment 2 that the purified protein has a main protein band at a position corresponding to a molecular weight of about 18,000–19,500 daltons on SDS-PAGE, and the fact that the purified protein is calculated to have a molecular weight of 18,199 daltons from the amino acid sequence of SEQ ID NO:6.

EXPERIMENT 4

Biological Activity

EXPERIMENT 4-1

IFN-γ Production by Immunocompetent Cell

Blood was sampled from a healthy volunteer by a heparinized syringe and diluted by 2-fold with serum free RPMI 1640 medium (pH 7.4). The diluted blood was overlaid on a ficoll commercialized by Pharmacia LKB Biotechnology AB, Uppsala, Sweden, followed by centrifugation to collect lymphocytes. These lymphocytes were washed with RPMI 1640 medium (pH 7.4) supplemented with 10 v/v t fetal bovine serum and suspended in a fresh preparation of the same medium to give a cell density of $5 \times 10^6$ cells/ml. The cell suspension was distributed to a 96-well microplate in a volume of 0.15 ml/well.

A purified protein obtained by the method in Experiment 1 was diluted with RPMI 1640 (pH 7.4) supplemented with 10 v/v % fetal bovine serum, and the dilution was distributed to the microplate in a volume of 0.05 ml/well. To the microplate was added a fresh preparation of the same buffer either with or without 2.5 μg/ml Con A or 50 units/ml of a recombinant human interleukin 2 in a volume of 0.05 ml/well, and the microplate was incubated at 37° C. for 24 hours in a 5 v/v % $CO_2$ incubator. After completion of the culture, 0.1 ml of a culture supernatant was sampled from each well and assayed for IFN-γ activity by conventional enzyme immunosorbent assay (EIA). As a control, a system free of the purified protein was provided and treated similarly as above. The results were in Table 1 where the IFN-γ content was assayed and expressed in terms of international unit (IU) with respect to "Gg23-901-530", an international standard for IFN-γ obtained from the National Institute for Health, Bethesda, Md., USA.

TABLE 1

| Protein concentration (ng/ml) | IFN-γ yield (IU/ml) | | |
|---|---|---|---|
| | Protein | Protein plus Con A | Protein plus interleukin 2 |
| 0 | <0.5 | <2 | <0.5 |
| 0.32 | <0.5 | 6 ± 2 | 2 ± 1 |
| 1.6 | 10 ± 2 | 70 ± 20 | 60 ± 20 |
| 8 | 140 ± 10 | 490 ± 80 | 570 ± 30 |
| 40 | 180 ± 20 | 620 ± 10 | 880 ± 50 |
| 200 | 260 ± 20 | 800 ± 20 | 1500 ± 400 |

Note: In the table, the wording "protein" means the present protein.

The results in Table 1 show that lymphocytes as an immunocompetent cell produced IFN-γ by the action of the present protein. As is evident from the results, the IFN-γ production is increased in the presence of interleukin 2 or Con A as a cofactor.

EXPERIMENT 4-2

Increase of Cytotoxicity by NK Cell

Blood was sampled from a healthy volunteer by a heparinized syringe and diluted with PBS by 2-fold. The dilution was overlaid on a ficoll, and the resultant was centrifuged to obtain a high density layer of lymphocytes. The lymphocytes were suspended in RPMI 1640 medium (pH 7.2) containing 10 μg/ml kanamycin, $5 \times 10^{-5}$ M 2-mercaptoethanol and 10 v/v fetal bovine serum, and the suspension was distributed to a 12-well microplate in a volume of 0.5 ml/well. A purified protein obtained by the method in Experiment 1 was appropriately diluted with a fresh preparation of the same buffer, and the dilution was distributed to the microplate in a volume of 1.5 ml/well, followed by adding to the microplate 0.5 ml/well of a fresh preparation of the same buffer either with or without 50 units/ml of a recombinant human interleukin 2, incubating the microplate at 37° C. for 24 hours in a 5 v/v % $Co_2$ incubator, and washing the resultant cells with PBS to obtain cultured lymphocytes containing NK cells as an effector cell. $1 \times 10^4$ cells/well aliquots of K-562 cells (ATCC CCL243), derived from human chronic myelocytic leukemia as a NK-cell susceptive target cell, which had been labelled with $^{51}Cr$ in conventional manner, were distributed to a 96-well microplate, and mixed with the above NK cells in a ratio of 2.5:1, 5:1 or 10:1 (=(effector cells):(target cells)). The microplate was incubated at 37° C. for 4 hours in a 5 v/v % $CO_2$ incubator, followed by counting the radio activity of each supernatant to count the dead target cells. In each system, the percentage (%) of the dead target cells with respect to the target cells used in this experiment was calculated for evaluating cytotoxicity. The results were in Table 2.

TABLE 2

| Protein concentration | Concentration of interleukin 2 | Cytotoxicity Effector cells/Target cells | | |
|---|---|---|---|---|
| (pM) | (unit/mL) | 2.5/1 | 5/1 | 10/1 |
| 0 | 0 | 19 | 36 | 59 |
| 0 | 10 | 28 | 44 | 61 |
| 0.5 | 0 | 22 | 41 | 63 |
| 0.5 | 10 | 31 | 54 | 69 |
| 5 | 0 | 28 | 49 | 66 |
| 5 | 10 | 36 | 58 | 71 |
| 50 | 0 | 29 | 53 | 67 |

TABLE 2-continued

| Protein concentration | Concentration of interleukin 2 | Cytotoxicity Effector cells/Target cells | | |
|---|---|---|---|---|
| (pM) | (unit/mL) | 2.5/1 | 5/1 | 10/1 |
| 50 | 10 | 42 | 62 | 72 |
| 500 | 0 | 33 | 56 | 84 |
| 500 | 10 | 57 | 78 | 96 |

Note: In the table, the symbol "pM" means $10^{-12}$ M, and the wording "protein" means the present protein.

The results in Table 2 show that the protein according to the present invention has a property of enhancing the cytotoxicity by NK cells. As is evident from the results, the cytotoxicity is more enhanced by the coexisting interleukin 2.

EXPERIMENT 4-3
Induction of LAK Cell Formation $1 \times 10^4$ cells/well aliquots of Raji cell (ATCC CCL86), a human Burkitt's lymphoma as an NK-cell non-susceptive target cell labelled with $^{51}$Cr in conventional manner were distributed to a 96-well microplate, and mixed with a cell suspension of the target cells and cultured lymphocytes containing LAK cells as an effector cell, prepared similarly by the method in Experiment 4-2 except for culturing 72 hours, in a ratio of 5:1, 10:1 or 20:1 (=(effector cells):(target cells)), followed by incubating the microplate at 37° C. for 4 hours in a 5 v/v % $Co_2$ incubator and counting the radio activity of each supernatant in conventional manner. Thereafter, the cytotoxicity (%) was calculated similarly as in Experiment 4–2. The results were in Table 3.

TABLE 3

| Protein concentration | Concentration of interleukin 2 | Cytotoxicity Effector cells/Target cells | | |
|---|---|---|---|---|
| (pM) | (unit/mL) | 5/1 | 10/1 | 20/1 |
| 0 | 0 | 12 | 23 | 31 |
| 0 | 10 | 14 | 25 | 35 |
| 0.5 | 0 | 14 | 24 | 34 |
| 0.5 | 10 | 18 | 32 | 42 |
| 5 | 0 | 16 | 26 | 37 |
| 5 | 10 | 21 | 36 | 50 |
| 50 | 0 | 22 | 41 | 49 |
| 50 | 10 | 26 | 52 | 56 |
| 500 | 0 | 27 | 44 | 61 |
| 500 | 10 | 33 | 59 | 72 |

Note: In the table, the symbol "pM" means $10^{-12}$ M, and the wording "protein" means the present protein.

The results in Table 3 show that the present protein has a property of inducing the LAK-cell formation. As is evident from these results, this induction is more enhanced by the coexisting interleukin 2.

EXPERIMENT 5
Acute Toxicity Test

A purified protein obtained by the method in Experiment 1 was injected percutaneously, orally or intraperitoneally into 8-week-old mice in conventional manner. As a result, the $LD_{50}$ of the protein was about one mg/kg mouse or higher independent of these administration routes. This evidences that the present protein is safe to incorporate into medicaments which are administrable to humans.

It is well known that IFN-γ deeply relates to the inhibition of bacterial infection and the propagation of malignant tumors, the regulation of human biophylaxis through the immunoregulatory function, and to the inhibition of immuno-globulin E antibody's production. As is described above, IFN-γ is now commercially available and used as an agent for human susceptive diseases, and the diseases to be treated, dose, administration, and safety are almost revealed. It is described in "*Cytokines in Cancer Therapy*", edited by Frances R. Balkwill, translated by Yoshihiko WATANABE, published by Tokyo-Kagaku-Dojin, Tokyo, Japan (1991) that treatments using killer cells such as NK- and LAK-cells are used as an antitumor immunotherapy and applied to human diseases, and reported that most of them exert a satisfactory therapeutic effect. Recently focussed is the relationship between the therapeutic effect and the augmentation of killer cells' cytotoxicity or the induction of killer cells' formation using cytokines. For example, T. Fujioka et al. reported in "*British Journal of Urology*", Vol.73, No.1, pp.23–31 (1994) that interleukin 2 strongly induced the formation of LAK cells in an antitumor immunotherapy using LAK cells and interleukin 2, and exerted a satisfactory effect on the metastasis of human cancer without substantially inducing serious toxicity and side effects.

Thus it is revealed that IFN-γ and killer cells closely relate to the treatment and the prevention of human diseases for complete cure and remission. Under these backgrounds as shown in the results in Experiments 4 and 5, the fact that the present protein induces the IFN-γ production by immuno-competent cells, enhances the NK cells' cytotoxicity, and induces the LAK cells' formation indicates that the present agent containing the protein can be administered to humans over a relatively long period of time and exerts a satisfactory therapeutic effect on the treatment and the prevention of IFN-γ and/or killer cell related diseases without substantially inducing serious side effects.

The following Examples explain the preferred embodiments of the present invention in more detail. Examples A-1 to A-8 are the preferred embodiments of the preparation of the present protein, and Examples B-1 to B-6 are the preferred embodiments of the present agent for susceptive diseases:

Example A-1
Preparation of Protein

New born hamsters were suppressed their immunoreaction in conventional manner by injecting a rabbit antiserum to hamster antithymus into the hamsters, transplanted to their dorsal subcutaneous tissues with about $5 \times 10^5$ cells/hamster of THP-1 cells (ATCC TIB202), a myelomonocytic cell line of a human acute leukemia, and fed for 3 weeks in conventional manner. Tumor masses, about 15 g weight each, subcutaneously formed in each hamster were extracted, suspended in physiological saline in conventional manner, and washed with PBS.

In accordance with the method by Matthew J. Kostura et al. in "Proceedings of the National Academy of Sciences of the United States of America", Vol.86, pp.5,227–5,231 (1989), the suspended cells were washed with 10-fold volumes of cold 20 mM Hepes buffer (pH 7.4) containing 10 mM potassium chloride, 1.5 mM magnesium chloride, 0.1 mM disodium ethylenediaminetetra-acetate, allowed to stand in 3-fold volumes of a fresh preparation of the same buffer, allowed to stand for 20 min under ice-chilled conditions, lyophilized at −80° C., and thawed to disrupt cells. The disrupted cells were centrifuged, and the supernatant was fed to a column packed with "DEAE-SEPHAROSE", a gel for ion-exchange chromatography commercialized by Pharmacia LKB Biotechnology AB, Uppsala, Sweden, followed by washing the column with 10 mM phosphate buffer (pH 6.6), fed with a gradient buffer of sodium chloride increasing stepwisely from 0 M to 0.5 M, and collecting fractions eluted at about 0.2 M sodium chloride.

The fractions were pooled, dialyzed against 10 mM phosphate buffer (pH 6.8), fed to a column packed with "DEAE 5PW", a gel for ion-exchange chromatography commercialized by Tosoh Corporation, Tokyo, Japan, which had been previously equilibrated with 10 mM phosphate buffer (pH 6.8), fed with a linear gradient buffer of sodium chloride increasing from 0 M to 0.5 M in 10 mM phosphate buffer (pH 6.8), and collected fractions eluted at about 0.2–0.3 M sodium chloride.

The resulting fractions were pooled and dialyzed against PBS. The dialyzed inner solution was fed to a cylindrical plastic column prepared by first packing a gel for immunoaffinity chromatography of a monoclonal antibody, which had been prepared according to the method disclosed in Japanese Patent Application No.58,240/95 applied by the present applicant, then washing with PBS. One hundred mM glycine-HCl buffer (pH 2.5) was fed to the column to effect fractionation, followed by collecting fractions containing a protein which induces the IFN-γ production by immunocompetent cells from the eluate, dialyzing the fractions against sterile distilled water, concentrating the dialyzed inner solution with a membrane filter, and lyophilizing the concentrate to obtain a solid purified protein. The yield was about 50 ng per hamster.

Example A-2
Preparation of Protein

New born nude mice were injected into their dorsal subcutaneous tissues with about 1×10$^6$ cells/nude mouse of KG-1 cells (ATCC CCL246), a myelomonocytic cell line derived from human acute myelomonocytic leukemia, and fed for 4 weeks in conventional manner. Tumor masses, about 20 g weight each, formed subcutaneously in each nude mouse were extracted and dispersed in physiological saline in conventional manner. The cells were washed and disrupted similarly as in Example A-1, and the resulting mixture was purified to obtain a purified protein which induces the IFN-γ production by immunocompetent cells in a yield of about 20 ng per nude mouse.

A portion of the purified protein was analyzed for amino acid sequence in accordance with the method in Experiments 2–4, revealing that the protein has the partial amino acid sequence of SEQ ID NO:1 near at the N-terminus and a similar molecular weight and biological activity as the protein in Experiment 1.

Example A-3
Preparation of Protein

HL-60 cells (ATCC CCL240), a myelomonocytic cell line derived from human acute promyelocytic leukemia, were suspended in RPMI 1640 (pH 7.4) placed in an about 10-ml plastic cylindrical diffusion chamber in which was installed a membrane filter with a diameter of 0.5 pm, then the chamber was intraperitoneally embedded in an aged rat. The rat was fed for 4 weeks in conventional manner, then the chamber was removed. The propagated cells in the chamber were collected, washed with physiological saline, and disrupted similarly as in Example A-1, followed by purifying the resulting mixture to obtain a purified protein which induces the IFN-γ production by immunocompetent cells. The yield was about 20 ng per rat.

A portion of the purified protein was analyzed for amino acid sequence in accordance with the method in Experiments 2–4, revealing that the protein has the partial amino acid sequence of SEQ ID NO:1 near at the N-terminus and has a similar molecular weight and biological activity to the protein in Experiment 1.

Example A-4
Preparation of Protein

THP-1 cells (ATCC TIB202), a myelomonocytic cell line derived from human acute monocytic leukemia, were suspended in RPMI 1640 medium (pH 7.2) supplemented with 10 v/v % fetal bovine serum to give a cell density of about 3×10$^5$ cells/ml, and cultured at 37° C. for 3 weeks in a 10 v/v % $CO_2$ incubator while replacing the medium with a fresh one. The propagated cells were separated from the resulting culture, washed with physiological saline, and disrupted similarly as in Example A-1, followed by purifying the resulting mixture to obtain a purified protein which induces the IFN-γ production in a yield of about 10 ng per litter of the culture.

A portion of the purified protein was analyzed for amino acid sequence in accordance with the method in Experiments 2–4, revealing that the protein has the partial amino acid sequence of SEQ ID NO:1 near at the N-terminus and has a similar molecular weight and biological activity to the protein in Experiment 1.

Example A-5
Preparation of Protein

New born hamsters were immunosuppressed by injecting a rabbit antithymus serum in conventional manner, injected to the dosal subcutaneous tissues with about 5×10$^5$ cells/head of A-253 cells (ATCC HTB41), an epidermoid carcinoma, submaxillary gland, human, and fed for 3 weeks in usual manner. Thereafter, the tumor masses formed subcutaneously, about 10 g weight in each hamster, were extracted, dispersed in physiological saline, and washed with PBS.

The propagated cells thus obtained were washed with 20 mM Hepes buffer (pH 7.4) containing 10 mM potassium chloride, 1.5 mM magnesium chloride, and 0.1 mM disodium ethylenediaminetetraacetate, suspended in a fresh preparation of the same buffer to give a cell density of about 2×10$^7$ cells/ml, disrupted by a homogenizer, and centrifuged to remove cell debris to obtain a supernatant, followed by concentrating the supernatant by a membrane for ultrafiltration to obtain a cell extract containing a protein which induces the interferon-γ production by immunocompetent cells. The extract was purified similarly as the method in Example A-1, concentrated, and lyophilized to obtain a solid purified protein in a yield of about 3 μg of per hamster.

The purified protein was sampled and analyzed in accordance with the methods in Examples 2–4 revealing that it has the amino acid sequence of SEQ ID NO:1 nearness to the N-terminus and has a similar molecular weight and biological activities to those of the protein in Experiment 1.

Example A-6
Preparation of Protein

A seed culture of A-253 cell was inoculated into RPMI 1640 medium (pH 7.4) supplemented with 10 v/v % fetal calf serum and cultured in conventional manner at 37° C. until forming a monolayer of cells. Thereafter, the cells were detached from the surface of the culture vessel used by using "TRYPSIN-EDTA", a trypsin commercialized by Gibuco BRL, NY, USA, and washed with PBS. In accordance with the method in Example A-1, the cells were disrupted, and the disrupted cells were purified and centrifuged to obtain a supernatant which was then incubated at 37° C. for 6 hours, purified, concentrated, and lyophilized to obtain a solid purified protein which induces the IFN-γ production by immunocompetent cells in a yield of about one μg per 10$^7$ cells.

The supernatant was sampled and analyzed in accordance with the method in Experiments 2–4 revealing that it has the amino acid sequence of SEQ ID NO:1 near at the N-terminus and has a similar molecular weight and biological activities to those of the protein in Experiment 1.

Example A-7
Preparation of Protein

A seed culture of A-253 cell was inoculated into RPMI 1640 medium (pH 7.4) supplemented with 10 v/v % fetal calf serum and cultured in conventional manner at 37° C. until forming a monolayer of cells. Thereafter, the culture medium was replaced with a serum-free RPMI 1640 medium (pH 7.4) supplemented with 10 IU/ml of a natural IFN-γ derived from KG-1 cell as an IFN-γ inducer, and incubated at 37° C. for 48 hours. The culture was centrifuged to obtain a supernatant which was then purified by the method in Example A-1, concentrated, and lyophilized to obtain a solid purified protein which induces the IFN-γ production by immunocompetent cells in a yield of about 5 ng per $10^7$ cells.

The supernatant was sampled and analyzed in accordance with the method in Experiments 2–4 revealing that it has the amino acid sequence of SEQ ID NO:1 nearness to the N-terminus and has a similar molecular weight and biological activities to those of the protein in Experiment 1.

Example A-8
Preparation of Protein

A purified protein obtained by the method in Example A-1 was dissolved in an adequate amount of sterile distilled water, and the solution was fed to a column packed with "ASAHIPAK® C4P-50 4E", a gel for high-performance liquid chromatography commercialized by Showa Denko K. K., Tokyo, Japan, which had been previously equilibrated with 0.1 v/v % aqueous trifluoroacetic acid, followed by washing the column with 0.1 v/v % aqueous trifluoroacetic acid and feeding to the column a linear gradient solution of acetonitrile increasing from 0 v/v % to 90 v/v % in a mixture solution of trifluoroacetic acid and acetonitrile at a flow rate of 60 ml/hour. Fractions containing a protein which induces the IFN-γ production by immunocompetent cells were collected from the eluted fractions, pooled, neutralized with 1 M aqueous tris solution (pH 11.2), and concentrated in conventional manner, followed by removing acetonitrile from the resulting concentrate to obtain a concentrated protein with a purity of at least 95% in a yield of about 10% by weight with respect to the material protein, d.s.b.

In accordance with the method in Experiment 2, the concentrated protein was sampled and analyzed for molecular weight, resulting in a single protein band, which induces an IFN-γ production, at a position corresponding to a molecular weight of 18,400±1,000 daltons. Another fresh sample was analyzed for amino acid sequence in accordance with the method in Experiments 3 and 4, revealing that it has the amino acid sequence of SEQ ID NO:3 and the one of SEQ ID NO:1 near at the N-terminus, more particularly, the one of SEQ ID NO:7, and further it has the amino acid sequence of SEQ ID NOs:4 and 5 as an internal fragment and exhibited a similar biological activity to the protein of Experiment 1 even when concentrated into a relatively high level.

Example B-1
Liquid

A purified protein obtained by the method in Example A-1 was dissolved in physiological saline containing one w/v % human serum albumin as a stabilizer, followed by sterilely filtering the solution to obtain a liquid.

The product with a satisfactory stability can be used as an injection, collunarium or nebula to treat and/or prevent susceptive diseases such as malignant tumors, viral diseases, bacterial infections, and immunopathies.

Example B-2
Dried Injection

A purified protein obtained by the method in Example A-2 was dissolved in physiological saline containing one w/v % of a purified gelatin as a stabilizer, and the solution was sterilely filtered in conventional manner. The sterile solution was distributed to vials by one ml and lyophilized, then the vials were cap sealed.

The product with a satisfactory stability can be used to treat and/or prevent susceptive diseases such as malignant tumors, viral diseases, bacterial infections, and immunopathies.

Example B-3
Dry Injection

A solid pharmaceutical was prepared similarly as in Example B-2 except for using a purified protein obtained by the method in Example A-5 and "TREHAOSE", a crystalline trehalose powder commercialized by Hayashibara Co., Ltd., Okayama, Japan, as a stabilizer.

The product with a satisfactorily stability can be advantageously used as a dry injection for treating and/or preventing malignant tumors, viral diseases, bacterial infections, and immunophathies.

Example B-4
Ointment

"HI-BIS-WAKO 104", a carboxyvinylpolymer commercialized by Wako Pure Chemicals, Tokyo, Japan, and "TREHAOSE", a crystalline trehalose powder commercialized by Hayashibara Co., Ltd., Okayama, Japan, were dissolved in sterile distilled water in respective amounts of 1.4 w/w % and 2.0 w/w %, and the solution was mixed to homogeneity with a purified protein obtained by the method in Example A-3, then adjusted to pH 7.2 to obtain a paste containing about one mg of a purified protein per g of the paste.

The product with a satisfactory spreadability and stability can be used to treat and/or prevent susceptive diseases such as malignant tumors, viral diseases, bacterial infections, and immunopathies.

Example B-5
Tablet

A purified protein obtained by the method in Example A-4 and "LUMIN (1-1'-1"-triheptyl-11-chinolyl(4).4.4'-penthamethinchynocyanine-1-1-dijodide)" as a cell activator were mixed to homogeneity with "FINETOSE®", an anhydrous crystalline a-maltose powder commercialized by Hayashibara Co., Ltd., Okayama, Japan, and the mixture was tabletted in conventional manner to obtain tablets, about 200 mg weight each, containing the purified protein and LUMIN in an amount of one mg each.

The product with a satisfactory swallowability, stability and cell-activating activity can be used to treat and/or prevent susceptive diseases such as malignant tumors, viral diseases, microbism, and immunopathies.

Example B-6
Agent for Adoptive Immunotherapy

Human monocytes were separated from peripheral blood of a patient with malignant lymphoma, suspended in RPMI 1640 medium (pH 7.2), which had been supplemented with 10 v/v % human AB serum and preheated at 37° C., to give a cell density of about 1×10$^6$ cells/ml, mixed with about 10 ng/ml of a purified protein obtained by the method in Example A-1 and about 100 units/ml of a recombinant human interleukin 2, and incubated at 37° C. for one week, followed by centrifugally collecting LAK cells.

The LAK cells exerted a strong cytotoxicity on lymphoma cells when introduced into the patient, and the therapeutic effect is significantly higher than that of the conventional adoptive immunotherapy using interleukin-2 alone. Cytotoxic T-cells, obtained by treating a patient's tumor tissue invasive lymphocyte instead of the patient's monocytes, showed a similar effect as in the LAK cells when reintroduced into the patient. The agent for adoptive immunotherapy can be suitably applied to solid tumors such as malignant nephroma, malignant melanoma, large intestinal cancer, and lung cancer.

As is described above, the present invention was made based on a novel protein which induces the IFN-γ production by immunocompetent cells and a discovery of human cells which produce the protein. The protein with a partly revealed amino acid sequence stably induces the IFN-γ production by immunocompetent cells. Therefore, the protein can be used widely as an IFN-γ inducer for IFN-γ production by culturing cells, and a therapeutic and/or prophylactic agent for IFN-γ susceptive diseases such as viral diseases, malignant tumors, and immunopathies which are susceptible to IFN-γ. The present agent for susceptive diseases which contains the protein as an effective ingredient exerts an outstanding effect on the treatment of inveterate diseases such as malignant tumors.

Because the protein has a strong IFN-γ production inducibility and has a relatively low toxicity, it induces generally a desired level of IFN-γ production with only a small amount and does not substantially cause serious side effects even when administered to patients at a relatively high dose. Therefore, the protein is advantageous in that it quickly induces a desired level of IFN-γ production without strictly controlling the dose. Especially, the present protein of human cell origin is advantageous in that it less causes side effects and less induces antibodies when administered to humans in the form of a pharmaceutical composition as compared with artificially produced polypeptides by the recombinant techniques.

The present protein having these satisfactory properties can be produced in a desired amount by the present process using human cells.

Thus the present invention with these significant functions and effects is a significant invention which greatly contributes to this field.

While there has been described what is at present considered to be the preferred embodiments of the invention, it will be understood the various modifications may be made therein, and it is intended to cover in the appended claims all such modifications as fall within the true spirit and scope of the invention.

We claim:

1. A process for producing a protein from a human cell capable of producing said protein, comprising propagating said human cell in culture or in a non-human animal, and collecting the produced protein from the propagated cells, wherein said protein has the amino acid sequence of SEQ ID No: 1 near or at the N-terminus, induces interferon-γ production by an immunocompetent cell, comprises the amino acid sequence of SEQ ID NO:3, and exhibits a molecular weight of 14,000–24,000 daltons as determined on sodium dodecyl sulfate polyacrvlamide gel electrophoresis (SDS-PAGE) in the presence of 2 w/v % dithiothreitol.

2. The process of claim 1, wherein said human cell is a human hematopoietic cell which produces said protein.

3. The process of claim 1, wherein the propagation step comprises transplanting said human cell to a warm-blooded animal excluding human, and propagating said human cell while allowing the cells to receive nutrients from the body fluid of the animal.

4. The process of claim 3, wherein said animal is a rodent.

5. The process of claim 1, wherein the collecting step is effected by one or more techniques selected from the group consisting of salting out, dialysis, filtration, concentration, separatory sedimentation, gel filtration chromatography, ion-exchange chromatography, hydrophobic chromatography, absorption chromatography, affinity chromatography, chromatofocusing, gel electrophoresis and isoelectrophoresis.

* * * * *

UNITED STATES PATENT AND TRADEMARK OFFICE
CERTIFICATE OF CORRECTION

PATENT NO.    : 6,242,255 B1  Page 1 of 1
DATED         : June 5, 2001
INVENTOR(S)   : Kenji Akita et al.

It is certified that error appears in the above-identified patent and that said Letters Patent is hereby corrected as shown below:

<u>Title page,</u>
Item [73], delete "Kegaku" and insert therefor -- Kagaku --.

Signed and Sealed this

Twentieth Day of August, 2002

Attest:

JAMES E. ROGAN
Attesting Officer          Director of the United States Patent and Trademark Office

```
                            SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Tyr Phe Gly Lys Leu Glu Ser Lys Leu Ser
1               5                   10

(2) INFORMATION FOR SEQ ID NO: 2:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
```

```
                          35                  40                  45
Ile Ser
    50

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Ser Ile Met Phe Thr Val Gln Asn Glu Asp
1               5                   10

(2) INFORMATION FOR SEQ ID NO: 4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Thr Ile Phe Ile Ile Ser Met Tyr Lys Asp Ser Gln Pro Arg
1               5                   10

(2) INFORMATION FOR SEQ ID NO: 5:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ile Ile Ser Phe Lys Glu Met Asn Pro Pro Asp Asn Ile Lys Asp Thr
1               5                   10                  15
Lys (2) INFORMATION FOR SEQ ID NO: 6:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: peptide (ix) FEATURE:
        (D) OTHER INFORMATION: "Xaa" in position 73 is either
            'Ile' or 'Thr'

(xi) SEQUENCE DESCRIPTION: SEQ ID NO: 6:

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
```

```
                35                  40                  45
Ile Ser Met Tyr Lys Asp Ser Gln Pro Arg Gly Met Ala Val Thr Ile
    50                  55                  60

Ser Val Lys Cys Glu Lys Ile Ser Xaa Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
                115                 120                 125

Lys Glu Arg Asp Leu Phe Lys Leu Ile Leu Lys Lys Glu Asp Glu Leu
                130                 135                 140

Gly Asp Arg Ser Ile Met Phe Thr Val Gln Asn Glu Asp
145                 150                 155
```

(2) INFORMATION FOR SEQ ID NO: 7:

(i) SEQUENCE CHARACTERISTICS:
        (A) LENGTH: 13 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 7:

```
Tyr Phe Gly Lys Leu Glu Ser Lys Leu Ser Val Ile Arg
1               5                   10
```

(2) INFORMATION FOR SEQ ID NO: 8:

(i) SEQUENCE CHARACTERISTICS:
        (A) LENGTH: 25 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 8:

```
Ile Ile Ser Phe Glu Glu Met Asp Pro Pro Glu Asn Ile Asp Asp Ile
1               5                   10                  15

Gln Ser Asp Leu Ile Phe Phe Gln Lys
                20                  25
```

(2) INFORMATION FOR SEQ ID NO: 9:

(i) SEQUENCE CHARACTERISTICS:
        (A) LENGTH: 18 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 9:

```
Gln Pro Val Phe Glu Asp Met Thr Asp Ile Asp Gln Ser Ala Ser Glu
1               5                   10                  15

Pro Gln
```

(2) INFORMATION FOR SEQ ID NO: 10:

(i) SEQUENCE CHARACTERISTICS:
    (A) LENGTH: 471 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 1..471

(xi) SEQUENCE DESCRIPTION: SEQ ID NO: 10:

```
AAC TTT GGC CGA CTT CAC TGT ACA ACC GCA GTA ATA CGG AAT ATA AAT    48
Asn Phe Gly Arg Leu His Cys Thr Thr Ala Val Ile Arg Asn Ile Asn
 1               5                  10                  15

GAC CAA GTT CTC TTC GTT GAC AAA AGA CAG CCT GTG TTC GAG GAT ATG    96
Asp Gln Val Leu Phe Val Asp Lys Arg Gln Pro Val Phe Glu Asp Met
                20                  25                  30

ACT GAT ATT GAT CAA AGT GCC AGT GAA CCC CAG ACC AGA CTG ATA ATA   144
Thr Asp Ile Asp Gln Ser Ala Ser Glu Pro Gln Thr Arg Leu Ile Ile
         35                  40                  45

TAC ATG TAC AAA GAC AGT GAA GTA AGA GGA CTG GCT GTG ACC CTC TCT   192
Tyr Met Tyr Lys Asp Ser Glu Val Arg Gly Leu Ala Val Thr Leu Ser
 50                  55                  60

GTG AAG GAT AGT AAA AYG TCT ACC CTC TCC TGT AAG AAC AAG ATC ATT   240
Val Lys Asp Ser Lys Xaa Ser Thr Leu Ser Cys Lys Asn Lys Ile Ile
 65                  70                  75                  80

TCC TTT GAG GAA ATG GAT CCA CCT GAA AAT ATT GAT GAT ATA CAA AGT   288
Ser Phe Glu Glu Met Asp Pro Pro Glu Asn Ile Asp Asp Ile Gln Ser
                 85                  90                  95

GAT CTC ATA TTC TTT CAG AAA CGT GTT CCA GGA CAC AAC AAG ATG GAG   336
Asp Leu Ile Phe Phe Gln Lys Arg Val Pro Gly His Asn Lys Met Glu
        100                 105                 110

TTT GAA TCT TCA CTG TAT GAA GGA CAC TTT CTT GCT TGC CAA AAG GAA   384
Phe Glu Ser Ser Leu Tyr Glu Gly His Phe Leu Ala Cys Gln Lys Glu
            115                 120                 125

GAT GAT GCT TTC AAA CTC ATT CTG AAA AAA AAG GAT GAA AAT GGG GAT   432
Asp Asp Ala Phe Lys Leu Ile Leu Lys Lys Lys Asp Glu Asn Gly Asp
130                 135                 140

AAA TCT GTA ATG TTC ACT CTC ACT AAC TTA CAT CAA AGT               471
Lys Ser Val Met Phe Thr Leu Thr Asn Leu His Gln Ser
145                 150                 155
```

(2) INFORMATION FOR SEQ ID NO: 11:

(i) SEQUENCE CHARACTERISTICS:
    (A) LENGTH: 157 amino acids
    (B) TYPE: amino acid
    (D) TOPOLOGY: linear (ii) MOLECULE TYPE: protein (ix) FEATURE:
    (D) OTHER INFORMATION: "Xaa" in position 70 is either 'Met' or 'Thr'

(xi) SEQUENCE DESCRIPTION: SEQ ID NO: 11:

```
Asn Phe Gly Arg Leu His Cys Thr Thr Ala Val Ile Arg Asn Ile Asn
 1               5                  10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile
         35                  40                  45
```

-continued

```
Tyr Met Tyr Lys Asp Ser Glu Val Arg Gly Leu Ala Val Thr Leu Ser
     50              55              60

Val Lys Asp Ser Lys Xaa Ser Thr Leu Ser Cys Lys Asn Lys Ile Ile
 65              70              75                       80

Ser Phe Glu Glu Met Asp Pro Pro Glu Asn Ile Asp Asp Ile Gln Ser
             85              90              95

Asp Leu Ile Phe Phe Gln Lys Arg Val Pro Gly His Asn Lys Met Glu
            100             105             110

Phe Glu Ser Ser Leu Tyr Glu Gly His Phe Leu Ala Cys Gln Lys Glu
        115             120             125

Asp Asp Ala Phe Lys Leu Ile Leu Lys Lys Lys Asp Glu Asn Gly Asp
    130             135             140

Lys Ser Val Met Phe Thr Leu Thr Asn Leu His Gln Ser
145             150             155
```